US011116644B2

United States Patent
Marrocco et al.

(10) Patent No.: US 11,116,644 B2
(45) Date of Patent: Sep. 14, 2021

(54) MULTIPLE EXPANSION STAGE INTERBODY DEVICES

(71) Applicant: MiRus LLC, Atlanta, GA (US)

(72) Inventors: Adam Marrocco, Kennesaw, GA (US); Josh Gunn, Atlanta, GA (US)

(73) Assignee: MiRus LLC, Atlanta, GA (US)

( * ) Notice: Subject to any disclaimer, the term of this patent is extended or adjusted under 35 U.S.C. 154(b) by 192 days.

(21) Appl. No.: 16/422,200

(22) Filed: May 24, 2019

(65) Prior Publication Data
US 2020/0054461 A1    Feb. 20, 2020

Related U.S. Application Data

(60) Provisional application No. 62/676,655, filed on May 25, 2018.

(51) Int. Cl.
 *A61F 2/44* (2006.01)
 *A61F 2/30* (2006.01)
 *A61F 2/46* (2006.01)

(52) U.S. Cl.
 CPC .......... *A61F 2/4455* (2013.01); *A61F 2/4425* (2013.01); *A61F 2002/3042* (2013.01); (Continued)

(58) Field of Classification Search
 CPC .................... A61F 2/442; A61F 2/4455; A61F 2002/30556; A61F 2002/30579; (Continued)

(56) References Cited

U.S. PATENT DOCUMENTS 6,126,689 A    10/2000  Brett
6,443,989 B1    9/2002  Jackson
(Continued)

FOREIGN PATENT DOCUMENTS

WO    2018/053403    3/2018

OTHER PUBLICATIONS

Globus Medical, RISE, titanium expandable lumbar fusion device, available at www.globusmedical.com/portfolio/rise/, last accessed May 20, 2019, 3 pages.
(Continued)

*Primary Examiner* — Brian A Dukert
(74) *Attorney, Agent, or Firm* — Meunier Carlin & Curfman LLC

(57) ABSTRACT

An example expandable interbody device can include a structural body having an upper endplate and a lower endplate. The device can include at least one wedge block and at least one linkage block arranged between the upper and lower endplates. The linkage block can include a plurality of linkages and a shear pin disposed at a respective proximal end of each of the linkages. The device can include a drive screw extending through the wedge and linkage blocks. The drive screw can be configured to rotate and drive the wedge block to expand the upper and lower endplates of the structural body from the closed position to an intermediate position. Additionally, the drive screw can be further configured to rotate and drive the linkage block to expand the upper and lower endplates of the structural body from the intermediate position to an open position.

20 Claims, 9 Drawing Sheets

(52) U.S. Cl.
CPC ............... *A61F 2002/30579* (2013.01); *A61F 2002/4688* (2013.01); *A61F 2310/00011* (2013.01)

(58) Field of Classification Search
CPC .. A61F 2002/30471; A61F 2002/30411; A61F 2002/30266; A61F 2002/443; A61B 17/8095
See application file for complete search history.

(56) References Cited

U.S. PATENT DOCUMENTS

| | | |
|---|---|---|
| 6,773,460 B2 | 8/2004 | Jackson |
| 6,849,093 B2 | 2/2005 | Michelson |
| 7,128,760 B2 | 10/2006 | Michelson |
| 7,731,751 B2 | 6/2010 | Butler et al. |
| 7,763,028 B2 | 7/2010 | Lim et al. |
| 7,828,849 B2 | 11/2010 | Lim |
| 7,951,199 B2 | 5/2011 | Miller |
| 8,043,381 B2 | 10/2011 | Hestad et al. |
| 8,105,382 B2 | 1/2012 | Olmos et al. |
| 8,486,149 B2 | 7/2013 | Saidha et al. |
| 8,491,659 B2 | 7/2013 | Weiman |
| 8,523,944 B2 | 9/2013 | Jimenez et al. |
| 8,574,300 B2 | 11/2013 | McManus et al. |
| 8,628,577 B1 | 1/2014 | Jimenez |
| 8,628,578 B2 | 1/2014 | Miller et al. |
| 8,632,593 B2 | 1/2014 | Suh et al. |
| 8,715,351 B1 | 5/2014 | Pinto |
| 8,795,366 B2 | 8/2014 | Varela |
| 8,845,731 B2 | 9/2014 | Weiman |
| 8,852,279 B2 | 10/2014 | Weiman |
| 8,888,854 B2 | 11/2014 | Glerum et al. |
| 8,894,711 B2 | 11/2014 | Varela |
| 8,940,049 B1 | 1/2015 | Jimenez et al. |
| 9,034,041 B2 | 5/2015 | Wolters et al. |
| 9,186,258 B2 | 11/2015 | Davenport et al. |
| 9,198,772 B2 | 12/2015 | Weiman |
| 9,233,007 B2 | 1/2016 | Sungarian et al. |
| 9,278,008 B2 | 3/2016 | Perloff et al. |
| 9,393,130 B2 | 7/2016 | Suddaby et al. |
| 9,445,919 B2 | 9/2016 | Palmatier et al. |
| 9,486,328 B2 * | 11/2016 | Jimenez ................. A61F 2/447 |
| 9,549,824 B2 | 1/2017 | McAfee |
| 9,554,918 B2 | 1/2017 | Weiman |
| 9,561,116 B2 | 2/2017 | Weiman et al. |
| 9,867,717 B2 | 1/2018 | Jimenez |
| 9,913,727 B2 * | 3/2018 | Thommen ............... A61F 2/447 |
| 9,924,972 B2 | 3/2018 | Yue |
| 2013/0190876 A1 | 7/2013 | Drochner et al. |
| 2016/0051384 A1 * | 2/2016 | Patel ......................... B21J 7/14 |
| | | 623/1.46 |
| 2016/0166396 A1 | 6/2016 | McClintock |
| 2017/0112630 A1 | 4/2017 | Kuyler et al. |
| 2017/0224505 A1 | 8/2017 | Butler et al. |
| 2017/0281361 A1 | 10/2017 | Jimenez et al. |
| 2017/0367842 A1 | 12/2017 | Predick et al. |
| 2019/0008995 A1 | 1/2019 | Roth |
| 2019/0133784 A1 | 5/2019 | Gunn et al. |

OTHER PUBLICATIONS

K2M Complex Spine Innovations, MOJAVE™ PL 3D Expandable Interbody System—K2M, available at https://www.k2m.com/products/product/mojave-pl-3d/, last accessed May 20, 2019, 1 page.

K2M Complex Spine Innovations, K2M Announces US Launch of First-to-Market 3D-Printed Expandable Interbody MOJAVE™ 3D Expandable Featuring Lamellar 3D Titanium Technology™, May 16, 2018, 2 pages.

Non-Final Office Action in connection to U.S. Appl. No. 16/147,986, dated Jan. 4, 2021.

\* cited by examiner

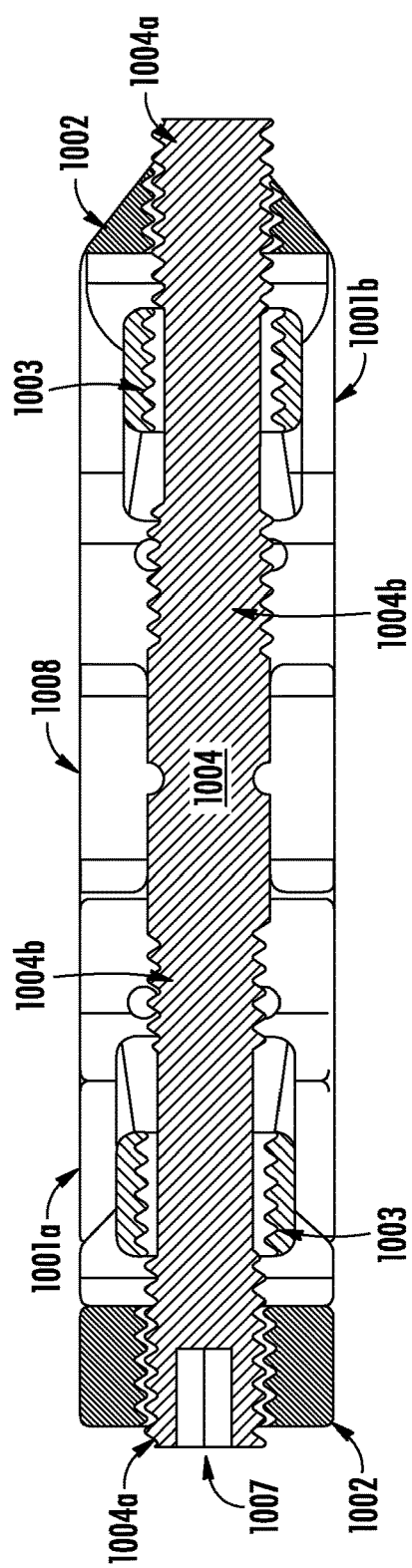
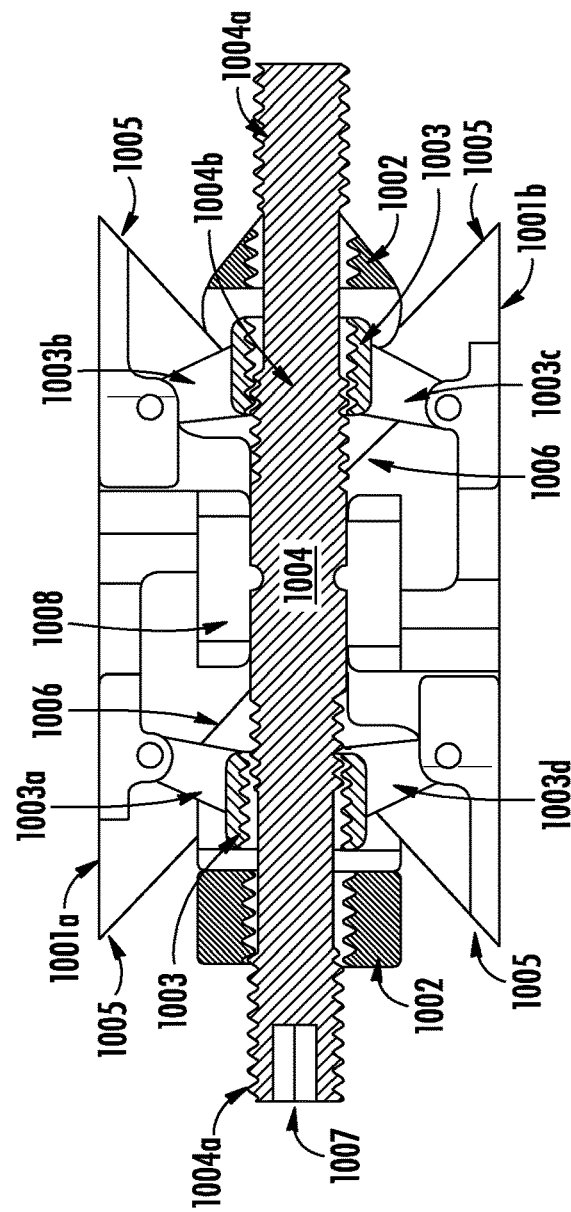
FIG. 6A
FIG. 6B

MULTIPLE EXPANSION STAGE INTERBODY DEVICES

CROSS-REFERENCE TO RELATED APPLICATIONS

This application claims the benefit of U.S. provisional patent application No. 62/676,655, filed on May 25, 2018, and entitled "Ramp-Linkage Hybrid Expandable Interbody," the disclosure of which is expressly incorporated herein by reference in its entirety.

BACKGROUND

An interbody device is a prosthesis used during spinal surgery. An interbody device is inserted into the space between spinal disks to provide stability. For example, an interbody device can be introduced between vertebrae of a patient's spine (e.g., in the disk space between adjacent vertebrae) for fixation with bone to immobilize the joint as part of a surgical treatment such as Transforaminal Lumbar Interbody Fusion (TLIF).

SUMMARY

Expandable interbody devices are described herein. An example expandable interbody device includes a structural body having an upper endplate and a lower endplate, where the upper and lower endplates are shaped to nest tightly in a closed position. The device includes at least one wedge block arranged between the upper and lower endplates of the structural body, and at least one linkage block arranged between the upper and lower endplates of the structural body. The at least one linkage block includes a plurality of linkages and a shear pin disposed at a respective proximal end of each of the linkages. The device also includes a drive screw extending through the at least one wedge block and the at least one linkage block. The drive screw is configured to rotate and drive the at least one wedge block to expand the upper and lower endplates of the structural body from the closed position to an intermediate position. In addition, the drive screw is further configured to rotate and drive the at least one linkage block to expand the upper and lower endplates of the structural body from the intermediate position to an open position.

Additionally, the shear pin is configured to prevent rotation of the upper and lower endplates about an axis of the drive screw.

Alternatively or additionally, the shear pin extends from the at least one linkage block into a portion of the at least one wedge block. Optionally, the shear pin is attached to the portion of the at least one wedge block.

Alternatively or additionally, the shear pin extends from the at least one linkage block without extending into a portion of the at least one wedge block.

Alternatively or additionally, the upper and lower endplates include first oblique surfaces and the at least one wedge block comprises second oblique surfaces. The first oblique surfaces are configured to engage with the second oblique surfaces to expand the upper and lower endplates of the structural body from the closed position to the intermediate position.

Alternatively or additionally, displacement of the at least one wedge block is configured to exclusively control expansion between the closed and intermediate positions, and displacement of the at least one linkage block is configured to exclusively control expansion between the intermediate and open positions. The at least one wedge block is configured to bear load during expansion between the closed and intermediate positions, and the at least one linkage block is configured to bear load during expansion between the intermediate and open positions. Optionally, the at least one wedge block is configured to disengage with the structural body at the intermediate position.

Alternatively or additionally, the drive screw includes a first threaded portion and a second threaded portion spaced apart from the first threaded portion. The first threaded portion of the drive screw is configured to engage with corresponding threads of the at least one wedge block. The second threaded portion of the drive screw is configured to engage with corresponding threads of the at least one linkage block.

In some implementations, the device further includes a plurality of wedge blocks arranged between the upper and lower endplates and on opposite sides of the structural body, where each of the wedge blocks is threaded in an opposite-handed direction. The drive screw is configured to rotate and drive the wedge blocks in opposite directions.

In some implementations, the device further includes a plurality of linkage blocks arranged between the upper and lower endplates and on opposite sides of the structural body, where each of the linkage blocks includes a plurality of linkages and a shear pin, respectively. Each of the linkage blocks is threaded in an opposite-handed direction, and the drive screw is configured to rotate and drive the linkage blocks in opposite directions.

Alternatively or additionally, the drive screw includes at least one driver hole.

Alternatively or additionally, the device further includes an alignment block configured to prevent rotation of the upper and lower endplates about an axis of the drive screw.

Alternatively or additionally, the device is made of a molybdenum-rhenium (MoRe) alloy (e.g., Mo47.5Re), a titanium (Ti) alloy, a titanium-molybdenum (TiMo) alloy, or a cobalt-chromium (CoCr) alloy.

Another example expandable interbody device includes a structural body having an upper endplate and a lower endplate, where the upper and lower endplates are shaped to nest tightly in a closed position. The device includes at least one wedge block arranged between the upper and lower endplates of the structural body, and at least one linkage block arranged between the upper and lower endplates of the structural body. The at least one wedge block defines opposing lateral sides and includes a slot arranged in at least one of the lateral sides. The at least one linkage block includes a plurality of linkages and a shear pin disposed at a respective proximal end of each of the linkages. The device also includes a drive screw extending through the at least one wedge block and the at least one linkage block. The drive screw is configured to rotate and drive the at least one wedge block to expand the upper and lower endplates of the structural body from the closed position to an intermediate position. In addition, the drive screw is further configured to rotate and deploy the linkages to expand the upper and lower endplates of the structural body from the intermediate position to an open position. The shear pin of the at least one linkage block is configured to traverse within the slot of the at least one wedge block.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 6A and 6B illustrate another example expandable interbody device according to an implementation described herein. FIG. 6A illustrates a cross-sectional view of the expandable interbody device in the closed position. FIG. 6B illustrates a cross-sectional view of the expandable interbody device in the open position.

FIG. 7A illustrates a side view of the expandable interbody device in the closed position. FIG. 7B illustrates a transparent side view of the expandable interbody device during a first (e.g., initial) stage of expansion. FIG. 7C illustrates a side view of the expandable interbody device during a second stage of expansion. FIG. 7D illustrates a side view of the expandable interbody device in the open position.

DETAILED DESCRIPTION

Figure 1:
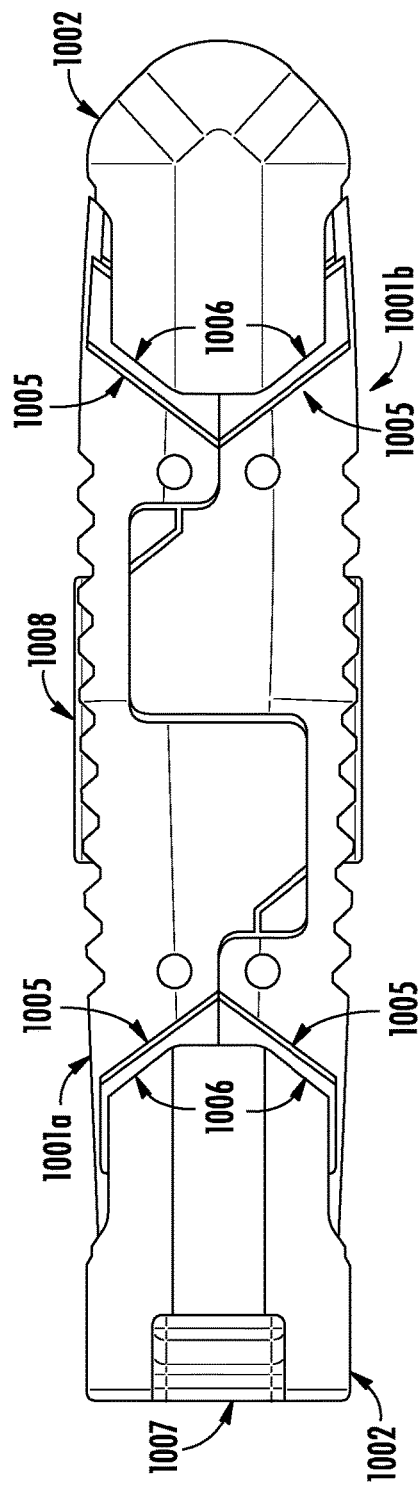
FIG. 1 illustrates a side view of an expandable interbody device in the closed position according to an implementation described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Multiple expansion stage interbody devices are described herein. An interbody device is a spine implant to position within an intervertebral space to facilitate bone fusion. More specifically, the interbody devices described herein are expandable to be used, for example, in a Transforaminal Lumbar Interbody Fusion (TLIF) approach. The interbody device can be inserted in the intervertebral space at an initial height profile, and through actuation of a control screw (e.g., turned clockwise), can cause the upper and lower bodies of the assembly to extend superiorly and inferiorly, respectively. The control screw can be turned in the counterclockwise direction to cause the interbody to collapse to its initial height to reposition or remove the interbody device. The interbody device described herein has a two-stage expansion mechanism; where at lower heights, the expansion is controlled by the ramps on proximal and distal blocks, and at a certain height, the upper and lower bodies disengage from the ramps and the expansion is controlled by the linkages assembled within the interbody device. The use of linkages allows expansion to be controlled by the length of the linkages, which pivot around a point. Because of this, the linkages can fit within the insertion profile of the interbody device, but are also able to pivot, extending beyond the initial profile if the length of the profile is larger than the height of the profile.

The interbody devices described herein facilitate a less invasive surgical procedure because the devices allow the implant to be inserted at a lower insertion profile and expanded to fit within the patient's intervertebral space. Additionally, the use of multiple expansion stages (e.g., ramps and linkages) allows for a greater range of expansion than conventional ramped devices, allowing the upper and lower bodies to extend beyond its initial height profile. The ramped portion also provides greater mechanical stability to mitigate the linkages' inherent weakness at more acute angles.

Referring now to FIGS. 1-5, an expandable interbody device is described. The device can include a structural body having an upper endplate 1001a and a lower endplate 1001b (collectively "endplates 1001"), where the upper and lower endplates 1001 are shaped to nest tightly in a closed position. Optionally, porous and/or roughened surfaces can be used on the endplates 1001, which can improve osseointegration. Example interbody devices that promote on-growth of bone are described in WO2018/053403, published Mar. 22, 2018, titled "INTERBODY FUSION DEVICES AND RELATED METHODS OF MANUFACTURE," the disclosure of which is expressly incorporated herein by reference in its entirety. In the closed position, the device is at its minimum height. This disclosure contemplates that a range of initial, minimum heights can be implemented in the design of the devices, allowing a range of expansion possibilities. Expansion of the device is accomplished through multiple stages (e.g., two stages) as described below. For example, the device can be actuated using a control screw (e.g., drive screw 1004 in FIGS. 1-5). During a first stage of expansion, actuation of the drive screw causes proximal and distal blocks (e.g., wedge blocks 1002 in FIGS. 1-5) to translate simultaneously in opposing horizontal directions, which results in the distraction of the superior endplate (e.g., upper endplate 1001a in FIGS. 1, 2, and 5) and the inferior endplate (e.g., lower endplate 1001b in FIGS. 1, 2, and 5) in opposing vertical directions. In the first stage, the device is expanded from the closed position to an intermediate position. During a second stage of expansion, actuation of the drive screw causes linkages (e.g., linkages 1003a-1003d in FIGS. 2, 4, and 5) to deploy, which results in the further distraction of the superior endplate (e.g., upper endplate 1001a in FIGS. 1, 2, and 5) and the inferior endplate (e.g., lower endplate 1001b in FIGS. 1, 2, and 5) in opposing vertical directions. In the second stage, the device is expanded from the intermediate position to an open position.

The endplates 1001 are configured to make direct contact with the patient's bone, e.g., with vertebral bodies in the section of the spine undergoing fixation/fusion. The endplates 1001 are designed to nest tightly with protrusions beyond center line to allow angled bosses to extend farther and thus allow more expansion of the structural body. Each of the endplates 1001 has faces oblique to the surfaces configured to contact the patient's bone (e.g., first oblique surfaces 1005 in FIGS. 1 and 2). The device can also include at least one wedge block 1002 arranged between the upper and lower endplates 1001 of the structural body. As shown in FIGS. 1-5, the device includes a plurality of wedge blocks 1002 (e.g. proximal and distal wedge blocks). Each of the wedge blocks 1002 has faces oblique to the top and bottom surfaces of the wedge blocks 1002, creating ramped surfaces (e.g., second oblique surfaces 1006 in FIGS. 1 and 2). The wedge blocks 1002 are support structures with the second oblique surfaces 1006 designed to accommodate the first oblique surfaces 1005 of the endplates 1001. As described below, when the wedge blocks 1002 travel, the second oblique surfaces 1006 interact with the corresponding first oblique surfaces 1005 of the endplates 1001 to cause expansion of the device.

Figure 2:
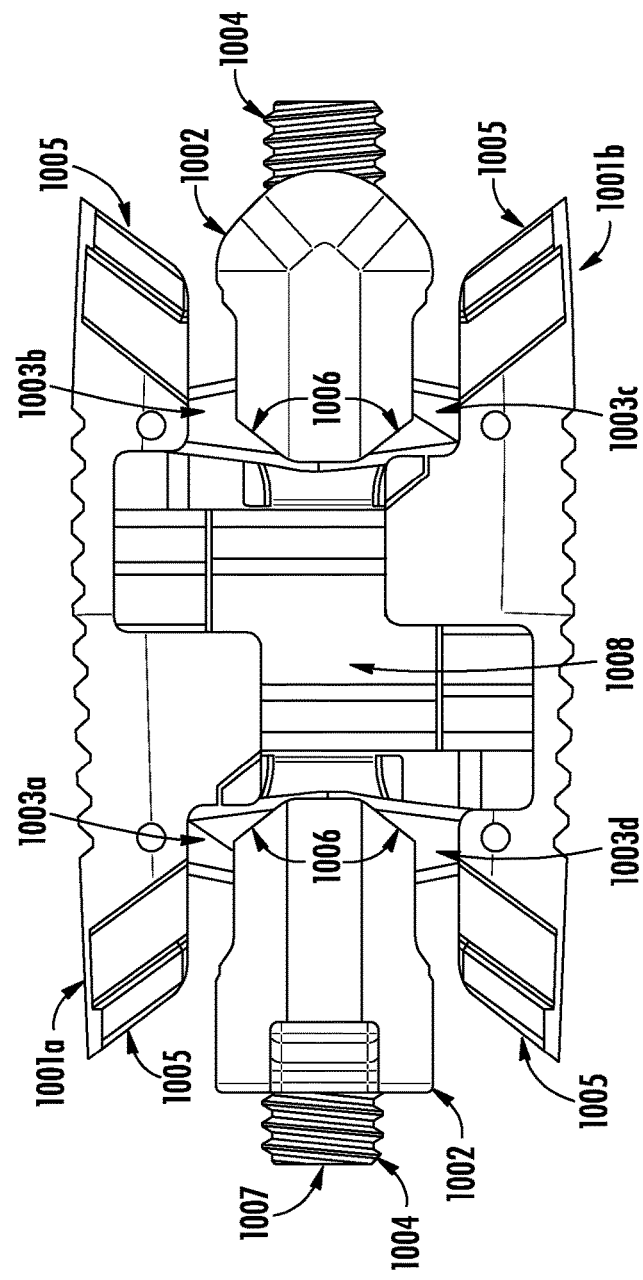
FIG. 2 illustrates a side view of the expandable interbody device of FIG. 1 in the open position.
Figure 3:
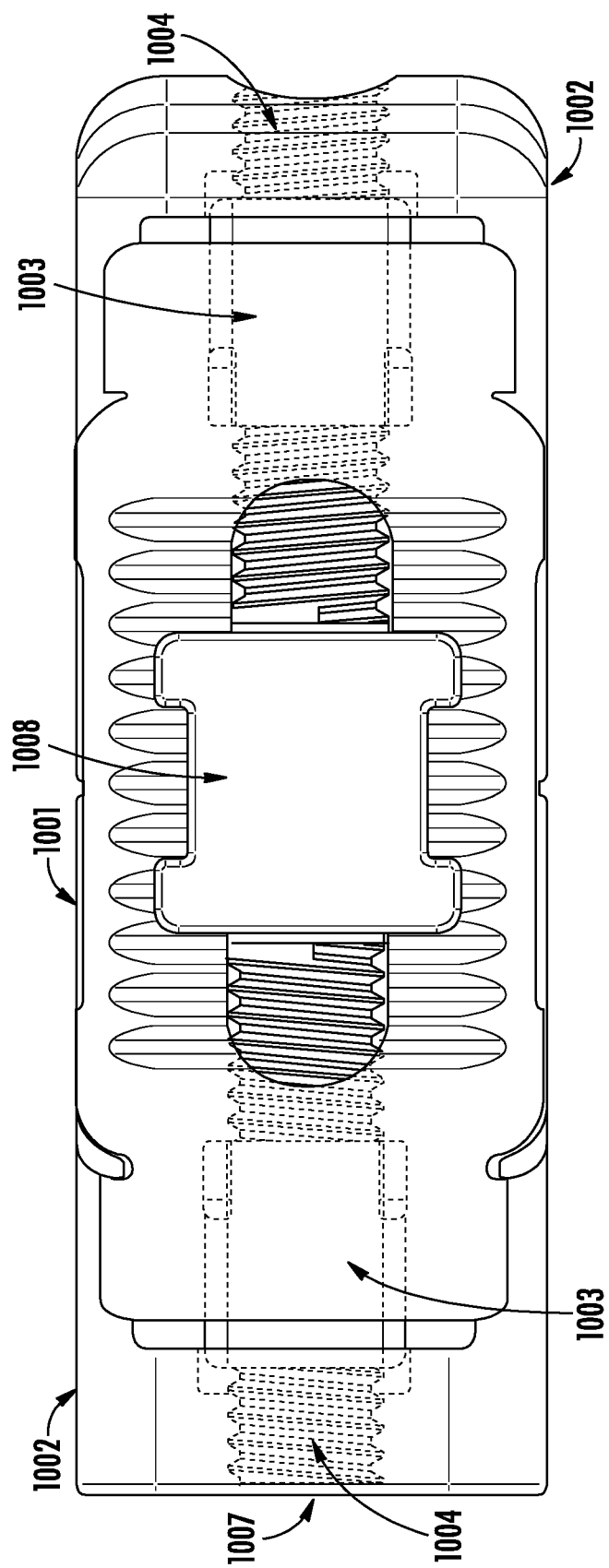
FIG. 3 illustrates a transparent top view of the expandable interbody device of FIG. 1 in the closed position.
Figure 4:
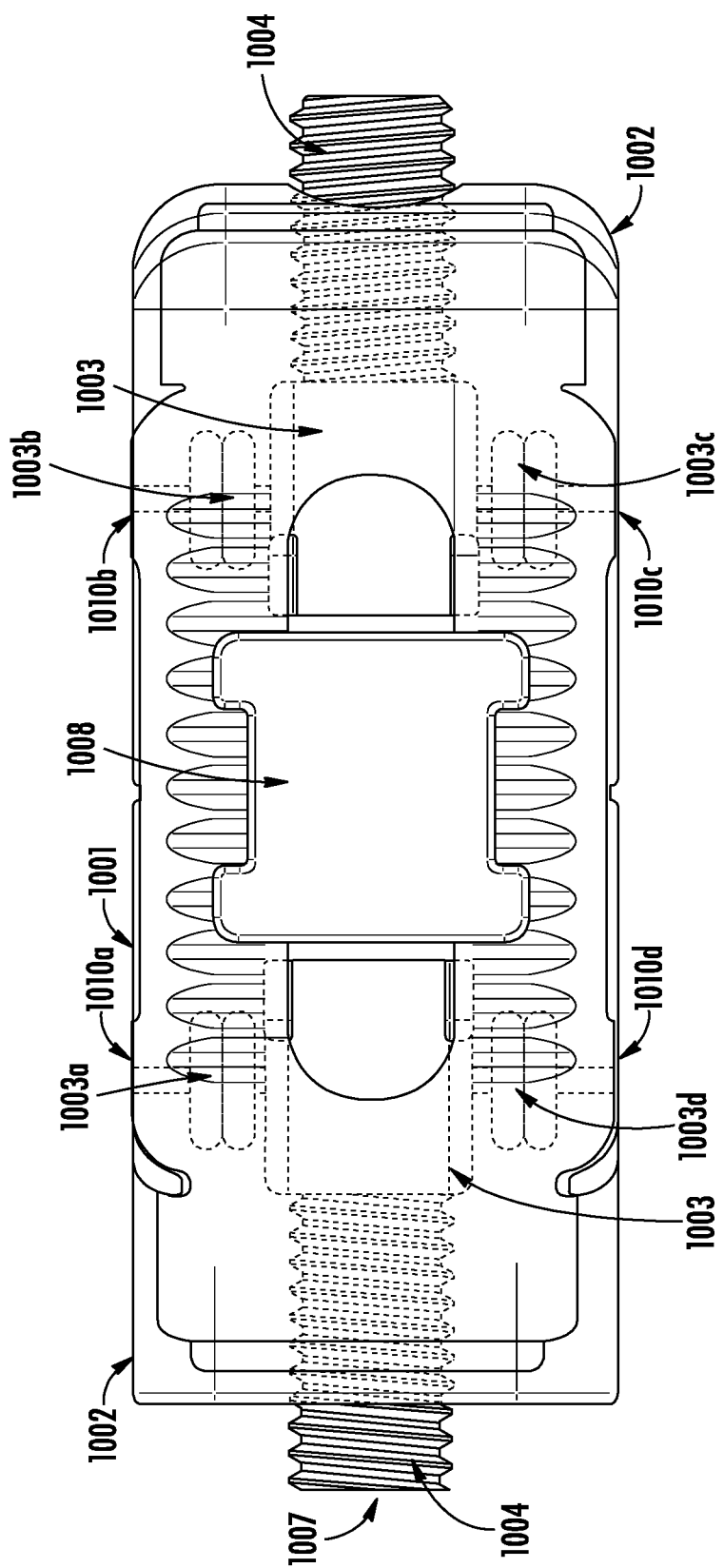
FIG. 4 illustrates a transparent top view of the expandable interbody device of FIG. 1 in the open position.

The device can also include at least one linkage block 1003 arranged between the upper and lower endplates 1001 of the structural body. As shown in FIGS. 2-5, the device includes a plurality of linkage blocks 1003 (e.g. proximal and distal linkage blocks). This disclosure contemplates that the wedge and linkage blocks can be integrated into a single block in some implementations, i.e., the linkage block can be a sub-portion of the wedge block. While in other implementations, this disclosure contemplates that the wedge and distal blocks can be separate and distinct blocks. The linkage blocks 1003 can include one or more linkages 1003a-1003d (e.g., levers). For example, the device shown in FIGS. 1-5 can include eight linkages (i.e., four linkages per linkage block 1003). Each of the linkages 1003a-1003d extends between a shear pin 1010, which is located at a proximal end of the linkage, and an endplate pin 1012, which is located at a distal end of the linkage. The linkages 1003a-1003d can be coupled to the wedge and/or linkage blocks and the endplates with the shear pins 1010 and the endplate pins 1012, respectively. The linkages 1003a-1003d rotate around a pivot point (e.g., the center of the shear pin) during actuation to expand the device. The device can optionally include four shear pins 1010a-1010d (i.e., two shear pins per linkage block, one on each opposing lateral side of the linkage block), which is shown in FIG. 4. Alternatively, the device can optionally include two shear pins 1010 (i.e., one shear pin per linkage block). Each of the shear pins 1010 can extend from a linkage block 1003 into a portion of a wedge block 1002, which is also shown in FIG. 4. For example, the shear pin 1010 can extend into a lateral side or portion of the wedge block 1002. Optionally, in some implementations, each of the shear pins 1010 is coupled with a portion of a wedge block 1002. Optionally, in some implementations, each of the shear pins 1010 can extend from a linkage block 1003 without extending into a portion of the wedge block 1002 (e.g., the shear pins are only part of the linkage block 1003). Accordingly, each of the shear pins 1010 can support load during second stage expansion. Additionally, each of the shear pins 1010 can prevent rotation of the endplates 1001 about the axis of the drive screw 1004. It should be understood that four shear pins (i.e., two per linkage block) is provided only as an example. This disclosure contemplates using one, two, or three shear pins with the device to prevent rotation of the endplates 1001.

Figure 10:
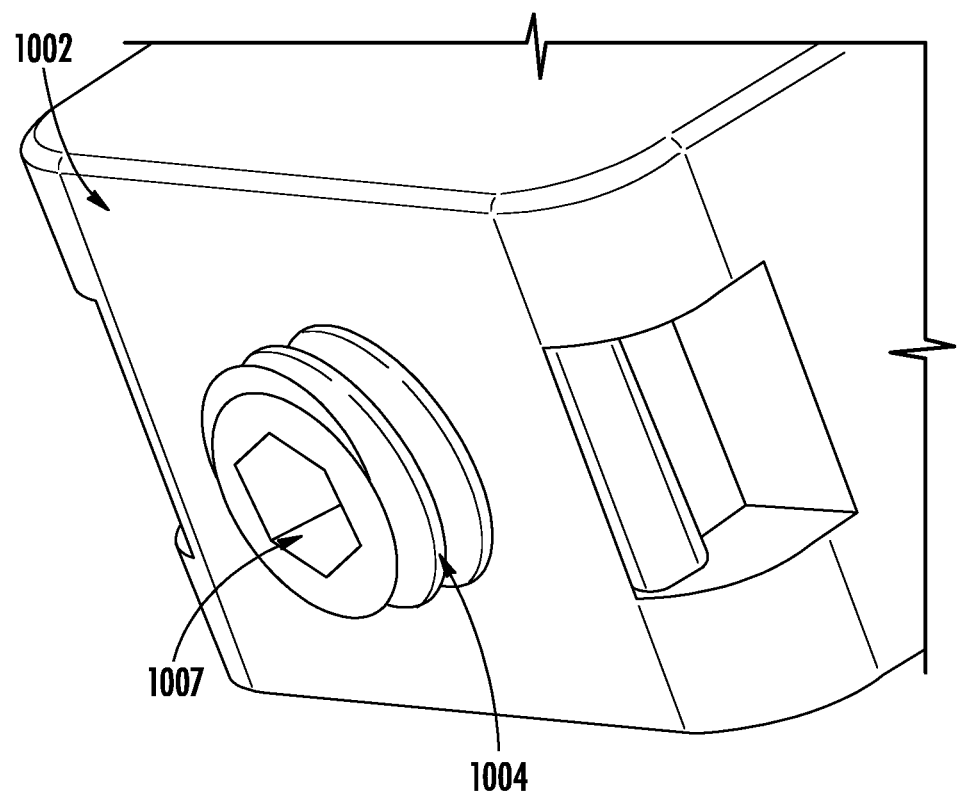
FIG. 10 illustrates a drive hole (e.g., insertion mechanism) of an expandable interbody device according to an implementation described herein.

Additionally, as described herein, the device can further include a drive screw 1004 extending through the wedge blocks 1002 and the linkage blocks 1003. The drive screw 1004 can include threads, and the wedge blocks 1002 and/or linkage blocks 1003 can include threads corresponding to the threads of the drive screw 1004. In this way, the threads of the drive screw 1004 can engage corresponding threads of the wedge blocks 1002 and/or linkage blocks 1003. In some implementations, only the wedge blocks 1002 include threads. In other implementations, both the wedge blocks 1002 and the linkage blocks 1003 include threads. Optionally, the pitches of the respective threads for controlling the wedge blocks 1002 and the linkage blocks 1003 are the same. Optionally, the pitches of the respective threads for controlling the wedge blocks 1002 and the linkage blocks 1003 are different. The drive screw 1004 can include a driver hole 1007 at one end of the drive screw 1004. The driver hole 1007 can be configured to accept the bit of a driver instrument or tool. Optionally, this disclosure contemplates that the drive screw 1004 can be operated from either end by providing a driver hole 1007 at both ends. FIG. 10 illustrates a close-up view of a driver hole 1007 (e.g., insertion mechanism) of an expandable interbody device. In FIG. 10, the drive screw 1004 extends through the wedge block 1002 of the device.

Figure 8:
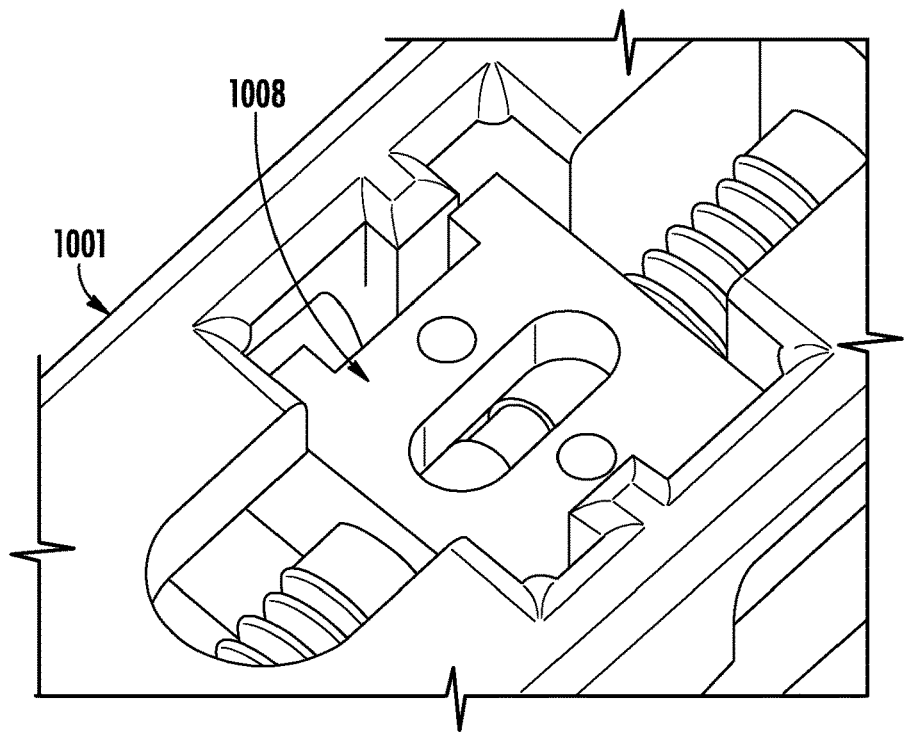
FIG. 8 illustrates an alignment block of an expandable interbody device according to an implementation described herein.

Referring again to FIGS. 1-5, the device can further include an alignment block 1008. The alignment block 1008 can guide expansion of the structural body. The alignment block 1008 can also prevent rotation of the endplates 1001 about the axis of the drive screw 1004. For example, the alignment block 1008 is located in the center of the device and prevents rotation of the endplates 1001, further constraining the expansion to one direction (i.e., the vertical direction). FIG. 8 illustrates a close-up view of an alignment block 1008 of an expandable interbody device. As shown in FIG. 8, the alignment block 1008 can include one or more notches that correspond to vertical grooves in the endplates 1001. This keeps the expansion of the structural body in the vertical direction and/or prevents rotation of the endplates about the axis of the drive screw.

Figure 9:
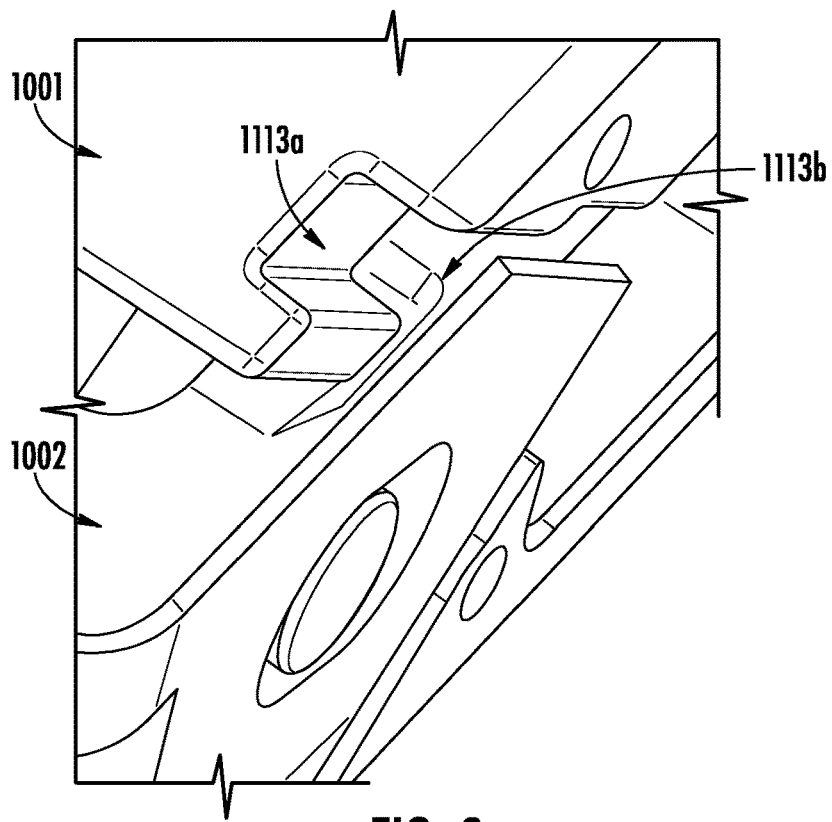
FIG. 9 illustrates a rail system of an expandable interbody device according to an implementation described herein.

Referring again to FIGS. 1-5, the first oblique surfaces 1005 of the endplates 1001 engage with the second oblique surfaces 1006 of the wedge blocks 1002 during the first stage of expansion. Optionally, in some implementations, the device can include a rail system. For example, the first oblique surfaces 1005 of the endplates 1001 can be coupled to the second oblique surfaces 1006 of the wedge blocks 1002 by the rail system. FIG. 9 illustrates a close-up view of a rail system of an expandable interbody device. As shown in FIG. 9, grooves 1113a located on oblique surfaces of the endplate 1001 can couple with bosses 1113b located on oblique surfaces of the wedge block 1002. The rail system (e.g., grooves 1113a, bosses 1113b) can more effectively constrain the expansion of the device to one direction (i.e., the vertical direction).

Referring again to FIGS. 1-5, the device includes a plurality of wedge blocks 1002 arranged between the upper and lower endplates 1001 and on opposite sides of the structural body (e.g., proximal and distal wedge blocks). Each of the wedge blocks 1002 can be threaded in an opposite-handed direction such that the drive screw 1004 is configured to rotate and drive the wedge blocks 1002 in opposite directions and towards the center of the device (when expanding the device). Additionally, as shown in FIGS. 2-5, the device can further include a plurality of linkage blocks 1003 arranged between the upper and lower endplates 1001 and on opposite sides of the structural body. In some implementations, the device can include eight linkages. For example, the device can include two linkages per articular point, e.g., four linkages on each side of the device for a total of eight. It should be understood that the number of linkages is provided only as an example. In some implementations, each of the linkage blocks 1003 can be threaded in an opposite-handed direction such that the drive screw 1004 is configured to rotate and drive the linkage blocks 1003 in opposite directions and towards the center of the device (when expanding the device).

Figure 5:
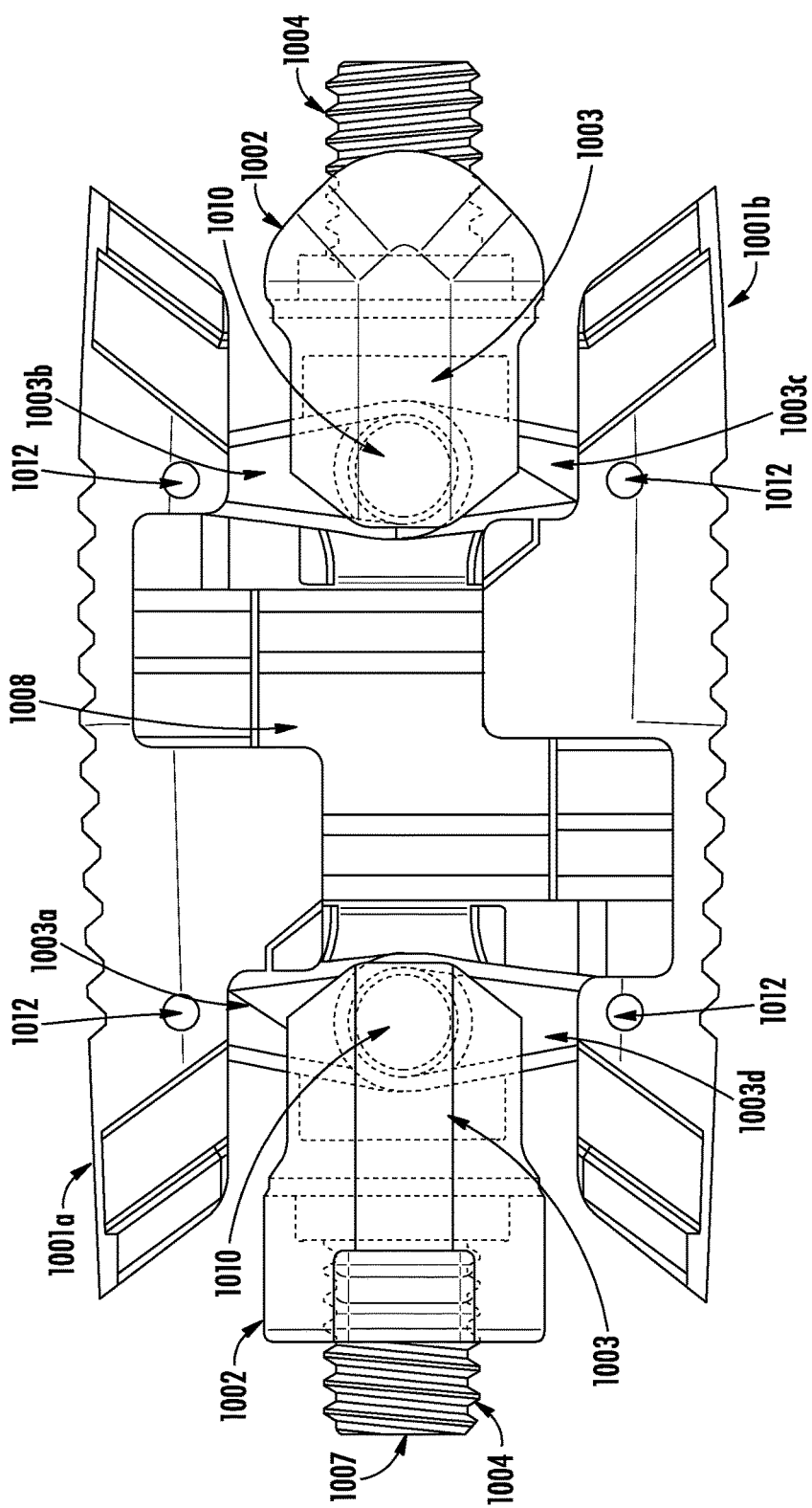
FIG. 5 illustrates a transparent side view of the expandable interbody device of FIG. 1 in the open position.

As described herein, the device has a dual stage mechanism (e.g., wedge blocks 1002 and linkage blocks 1003) controlled by rotation of the drive screw 1004. In a first stage, the device expands between the closed and intermediate positions. Expansion in the first stage is controlled exclusively using the wedge blocks 1002. To accomplish this, the threads of the drive screw 1004 are timed such that the wedge blocks 1002 are engaged by the drive screw 1004 during the first stage. The threads can be timed such that the wedge blocks 1002 move together and in opposite directions. The drive screw 1004 is therefore configured to rotate and drive the wedge blocks 1002, which moves the upper and lower endplates 1001 of the structural body from a closed position to an intermediate position. FIGS. 1 and 3 illustrate the device in the closed position, while FIGS. 2, 4, and 5 illustrate the device in the open position. As shown in FIGS. 1 and 2, the first oblique surfaces 1005 are included on the upper and/or lower endplates 1001, and the second oblique surfaces 1006 are included on the wedge blocks 1002. The second oblique surfaces 1006 can be configured to interact with the first oblique surfaces 1005 to expand the upper and lower endplates 1001 of the structural body as the wedge blocks 1002 translate due to rotation of the drive screw 1004. In other words, the wedge blocks 1002 control expansion in the first stage by physically forcing the endplates 1001 apart. Optionally, the first oblique surfaces 1005/second oblique surfaces 1006 can function as a ratchet, e.g., such that the structural body expands (or contracts) in a step-wise manner as the drive screw 1004 is rotated. Optionally, the first oblique surfaces 1005/second oblique surfaces 1006 can include a rail system to further constrain expansion. Once the device reaches the intermediate position, the wedge blocks 1002 can optionally disengage with the structural body (e.g., no more contact with the structural body). At this point, expansion control is transferred to the linkage blocks 1003 as described below. Additionally, during the first stage, the linkages 1003a-1003d are neither load supporting nor impacting/controlling expansion.

In a second stage, the device expands between the intermediate and open positions. Expansion in the second stage is controlled exclusively using the linkage blocks 1003, for example, by deployment of the linkages 1003a-1003d. Horizontal translation of the proximal end of the linkages 1003a-1003d can be limited so that the endplates 1001 cannot re-engage with the wedge blocks 1002 during the second stage. This can be accomplished in different ways. For example, in some implementations, the linkage blocks 1003 are provided with threads corresponding to threads of the drive screw 1004 such that displacement of the linkage blocks 1003 is controlled directly by a pitch of the threads of the drive screw 1004. This is described in detail with regard to FIGS. 6A-6B. In other implementations, deployment of the linkages 1003a-1003d is controlled by interaction between slots in the wedge blocks 1002 and the shear pins 1010. This is described in detail with regard to FIGS. 7A-7D.

Referring again to FIGS. 1-5, expansion during the second stage is described. FIGS. 1 and 3 illustrate the device in the closed position, while FIGS. 2, 4, and 5 illustrate the device in the open position. As shown in FIGS. 2, 4, and 5, the linkage blocks 1003 include one or more linkages 1003a-1003d (e.g., levers) that are configured to displace the endplates 1001 when the linkage blocks 1003 are engaged by the drive screw 1004. A linkage (e.g., one of linkages 1003a-1003d) is attached between a linkage block (e.g., one of linkage blocks 1003) with the shear pin (e.g., one of shear pins 1010) and an endplate 1001 (e.g., one of endplates 1001) with the endplate pin (e.g., one of endplate pins 1012). The linkage blocks 1003 control expansion in the second stage by moving the endplates 1001 with the linkages 1003a-1003d. The dual stage expansion described above (e.g., using both wedge and linkage blocks) allows the device to expand farther than conventional devices. For example, by using the linkage blocks 1003, the device can expand double its initial height, which would be a limiting factor for devices that use only wedge blocks as a drive mechanism. Additionally, since the linkages 1003a-1003d experience higher stresses at the attachment to the device at more acute angles of the linkages, the wedge blocks 1002 are bearing the load during the first expansion stage (e.g., when the linkages 1003a-1003d are most acute). Once the expansion has reached its maximum height facilitated by the wedge blocks, the wedge blocks 1002 disengage and the linkage blocks 1003 provide for additional expansion of the device.

Referring now to FIGS. 6A-6B, another example expandable interbody device is described. FIG. 6A illustrates a cross-sectional view of the expandable interbody device in the closed position. FIG. 6B illustrates a cross-sectional view of the expandable interbody device in the open position. The device includes endplates 1001a and 1001b (collectively "endplates 1001"), wedge blocks 1002, and linkage blocks 1003 (and linkages 1003a-1003d). As shown in FIGS. 6A-6B, the wedge blocks 1002 and linkage blocks 1003 are concentric with the drive screw 1004. A drive screw 1004 extends through the wedge blocks 1002 and the linkage blocks 1003, and a driver hole 1007 is provided at one end of the drive screw 1004. An alignment block 1008 is also provided in the device. Except as provided below, the device shown in FIGS. 6A and 6B operates similarly as described above with regard to FIGS. 1-5. For example, during a first stage of expansion, the wedge blocks 1002 exclusively control expansion of the device. To accomplish this, the drive screw 1004 is actuated to drive the wedge blocks 1002, which move together and in opposite directions. For example, when the device is expanded, the wedge blocks 1002 move towards one another (e.g., one wedge block moves to the left and the other wedge block moves to the right). It should be understood that when the device is collapsed, the wedge blocks 1002 move away from one another (e.g., one wedge block moves to the left and the other wedge block moves to the right). The drive screw 1004 includes a first threaded portion 1004a and a second threaded portion 1004b. The first threaded portion 1004a is spaced apart from the second threaded portion 1004b. As described herein, the first threaded portion 1004a engages with the wedge block 1002, and the second threaded portion 1004b engages with the linkage block 1003. The second oblique surfaces 1006 of the wedge blocks 1002 interact with the first oblique surfaces 1005 of the endplates 1001 to expand the upper and lower endplates 1001 of the structural body as the wedge blocks 1002 translate due to rotation of the drive screw 1004. Thus, the wedge blocks 1002 control expansion in the first stage by physically forcing the endplates 1001 apart.

On the other hand, during a second stage of expansion, the linkage blocks 1003 exclusively control expansion of the device. The drive screw 1004 is actuated to drive the linkage blocks 1003, which move together and in opposite directions. For example, when the device is expanded, the linkage blocks 1003 move towards one another (e.g., one linkage block moves to the left and the other linkage block moves to the right). It should be understood that when the device is collapsed, the linkage blocks 1003 move away from one another (e.g., one linkage block moves to the left and the other linkage block moves to the right). To accomplish this, both the wedge blocks 1002 and the linkage blocks 1003 are provided with threads corresponding to those of the drive screw 1004. For example, the drive screw 1004 includes the first threaded portion 1004a and the second threaded portion 1004b, which is spaced apart from the first threaded portion 1004a. The portion of the drive screw 1004 between the first threaded portion 1004a and the second threaded portion 1004b (i.e., the unthreaded portion) does not have any threads. The first threaded portion 1004a engages with the wedge block 1002 during the first stage (see FIG. 6A), and the second threaded portion 1004b engages with the linkage block 1003 during the second stage (see FIG. 6B). The unthreaded portion of the drive screw 1004 is aligned with the linkage blocks 1003 and the wedge blocks during the first and second stages, respectively. In other words, the respective first and second threaded portions are used to drive the wedge and linkage blocks, respectively. The threads of the second threaded portion 1004b of the drive screw 1004 are timed such that the linkage blocks 1003 are engaged by the drive screw 1004 during the second stage. The threads can be timed such that the linkage blocks 1003 move together and only after initial expansion by the wedge blocks 1002. The drive screw 1004 can therefore be configured to engage the linkage blocks 1003 at the intermediate position, and at this point, the shear pins (not shown in FIGS. 6A and 6B) take on load as the linkages deploy. As described above, a shear pin (e.g., shear pins 1010 in FIGS. 4 and 5) can extend through the proximal end of each of the linkages 1003a-1003d to a portion of the wedge block 1002 (e.g., to a lateral side of the wedge block 1002). The device in FIGS. 6A-6B includes two shear pins, each of which extends through the proximal end of four linkages (e.g., two on each lateral side of a linkage block). The shear pin can be anchored or attached to the wedge block 1002. For example, the shear pin can be coupled with or within the lateral side of the wedge block 1002. Then, as the drive screw 1004 is further actuated, it rotates and drives the linkage blocks 1003, which further expands the upper and lower endplates 1001 of the structural body from the intermediate position to an open position. In this way, the linkage blocks 1003 are directly controlled by the pitch of the second threaded portion 1004b of the drive screw 1004. Additionally, the unthreaded portion of the drive screw 1004 allows the drive screw 1004 to travel without resistance, which prevents loading of the linkages 1003a-1003d during the first stage of expansion. In some implementations, the first threaded portion 1004a has the same pitch as the second threaded portion 1004b, while in other implementations, the first threaded portion 1004a has a different pitch than the second threaded portion 1004b.

Figure 7A:
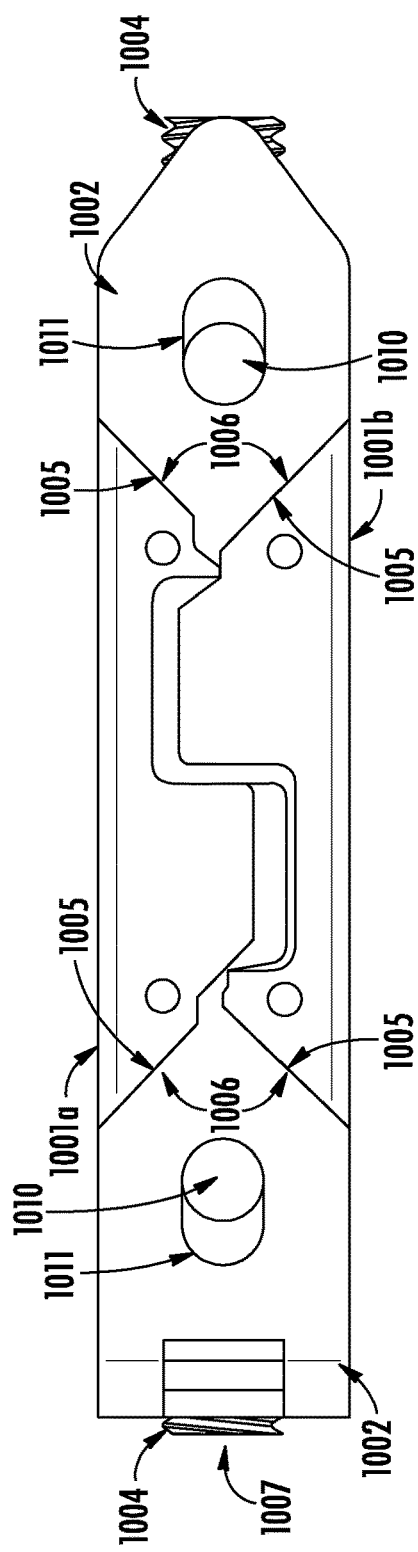
FIGS. 7A-7D illustrate another example expandable interbody device according to an implementation described herein.
Figure 7B:
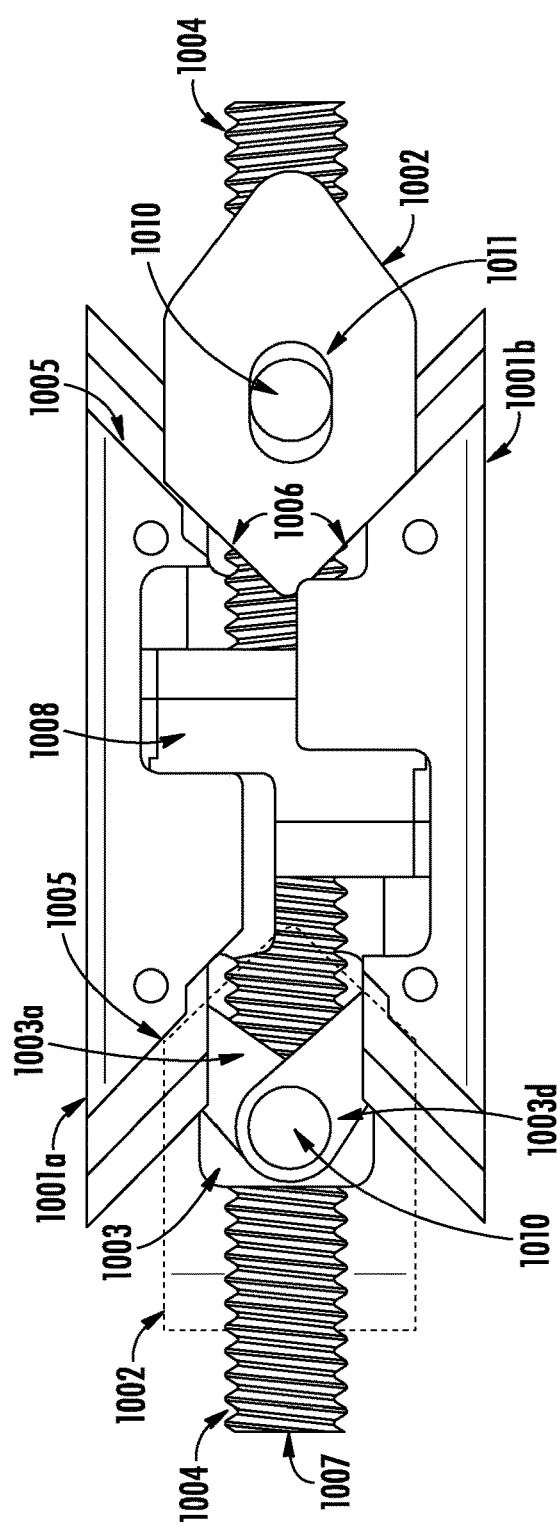
Figure 7C:
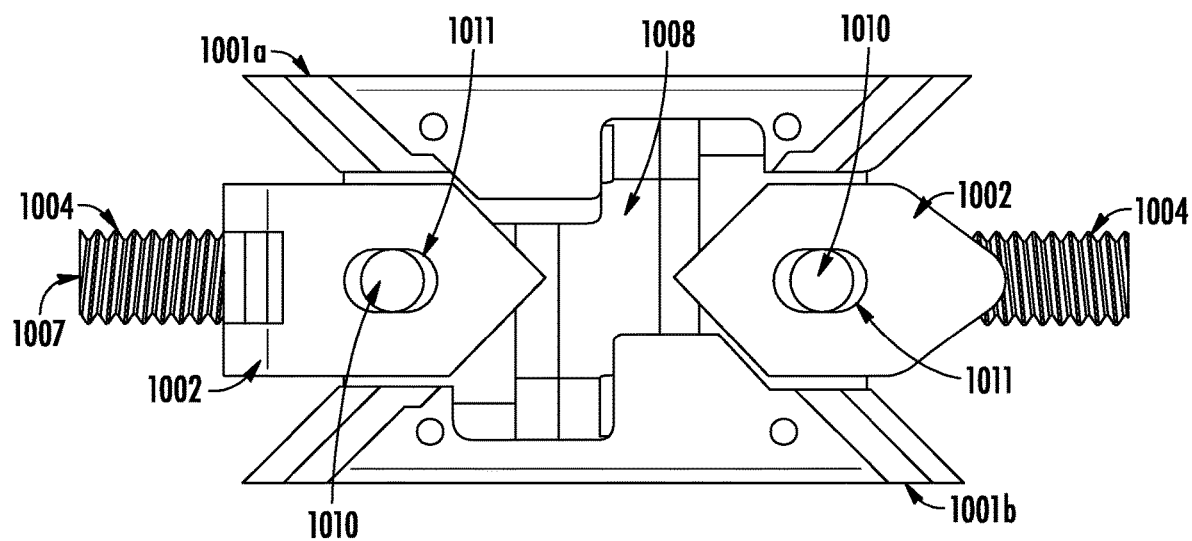
Figure 7D:
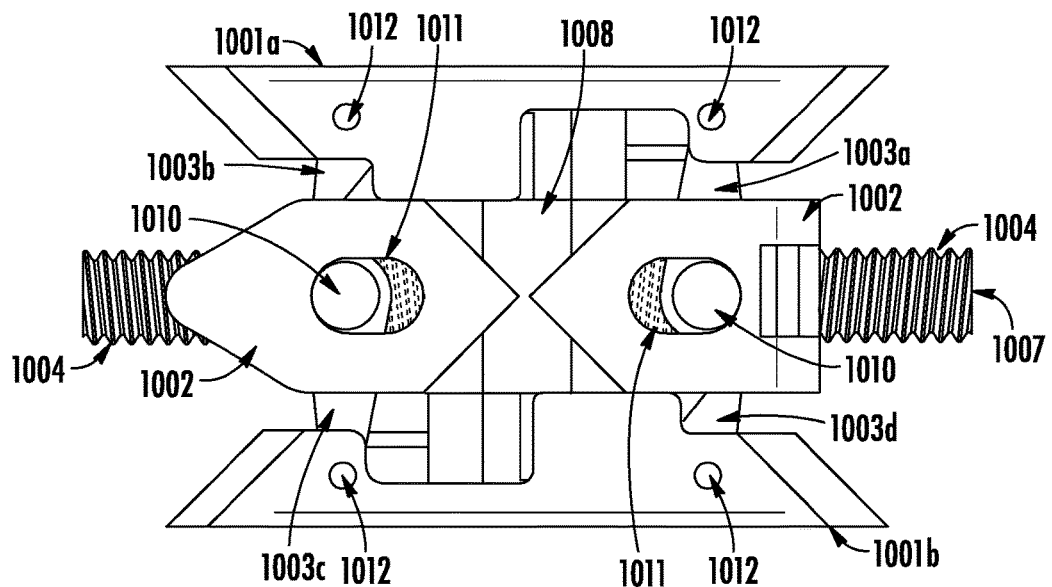

Referring now to FIGS. 7A-7D, another example expandable interbody device is described. FIG. 7A illustrates a side view of the expandable interbody device in the closed position. FIG. 7B illustrates a transparent side view of the expandable interbody device during a first (e.g., initial) stage of expansion. FIG. 7C illustrates a side view of the expandable interbody device during a second stage of expansion. FIG. 7D illustrates a side view of the expandable interbody device in the open position. The device includes endplates 1001a and 1001b (collectively "endplates 1001"), wedge blocks 1002, and linkage blocks 1003 (and linkages 1003a-1003d). A drive screw 1004 extends through the wedge blocks 1002 and the linkage blocks 1003, and a driver hole 1007 is provided at one end of the drive screw 1004. As shown in FIGS. 7A-7D, the wedge blocks 1002 and linkage blocks 1003 are concentric with the drive screw 1004. An alignment block 1008 is also provided in the device. Except as provided below, the device shown in FIGS. 7A-7D operates similarly as described above with regard to FIGS. 1-5. For example, during a first stage of expansion, the wedge blocks 1002 exclusively control expansion of the device. To accomplish this, the drive screw 1004 is actuated to drive the wedge blocks 1002, which move together and in opposite directions. For example, when the device is expanded, the wedge blocks 1002 move towards one another (e.g., one wedge block moves to the left and the other wedge block moves to the right). It should be understood that when the device is collapsed, the wedge blocks 1002 move away from one another (e.g., one wedge block moves to the left and the other wedge block moves to the right). The second oblique surfaces 1006 of the wedge blocks 1002 interact with the first oblique surfaces 1005 of the endplates 1001 to expand the upper and lower endplates 1001 of the structural body as the wedge blocks 1002 translate due to rotation of the drive screw 1004. Thus, the wedge blocks 1002 control expansion in the first stage by physically forcing the endplates 1001 apart.

On the other hand, during a second stage of expansion, the linkage blocks 1003 exclusively control expansion of the device. The drive screw 1004 is actuated to deploy the linkages 1003a-1003d, which are attached to the endplates 1001 by endplate pins 1012 and to the linkage blocks 1003 by shear pins 1010 as described above. To accomplish this, a shear pin 1010 can extend through the proximal end of each of the linkages 1003a-1003d and through a portion of the wedge block 1002. One shear pin 1010 can extend through the proximal end of each of the linkages of each linkage block 1003. For example, the device in FIGS. 7A-7D includes two shear pins, each of which extends through the proximal end of four linkages (e.g., two linkages on each lateral side of a linkage block). Additionally, a slot 1011 is arranged in the lateral side of the wedge block 1002. The device in FIGS. 7A-7D includes four slots 1011 (e.g., two on each lateral side of a wedge block and/or one slot for each end of the shear pin). The size and/or shape of the slot 1011 (e.g., outer diameter of the slot 1011) is designed such that the shear pin 1010 can traverse within the slot 1011. For example, in the closed position shown in FIG. 7A, the shear pins 1010 are located within the slots 1011 and centrally with respect to the device. During the first stage of expansion shown in FIG. 7B, the shear pins 1010 traverse within the slots 1011 outwardly with respect to the device as the drive screw 1004 is actuated. Eventually as shown in FIGS. 7C and 7D, the shear pins 1010 reach the outermost edge of the slots 1011 near the intermediate position. As a result, further actuation of the drive screw 1004 drives the shear pins 1010 causing the linkages 1003a-1003d to deploy. As described herein, the shear pins 1010 take on load as they deploy and expand the device between the intermediate and open positions. Optionally, in some implementations, the drive screw 1004 can include a first threaded portion and a second threaded portion as described with regard to FIGS. 6A and 6B. As described herein, the first threaded portion can engage with the wedge block 1002, and the second threaded portion can engage with the linkage block 1003.

Although examples are provided for expanding the device, it should be understood that the drive screw can be rotated in the opposite direction to contract or collapse the device. For example, the linkage blocks can be used to collapse the device from the open position to the intermediate position, and the wedge blocks can be used to collapse the devices from the intermediate position to the closed position. Additionally, it should be understood that the device can be expanded to a desired height and stay at this desired height during and after implantation. The desired height is independent of the intermediate and/or fully open positions. For example, some patients may require the device to be expanded to a height less than the intermediate position, while some patients may require the device to be expanded to a height greater than the intermediate position. In other words, the device does not need to be expanded to the fully open position (or even the intermediate position) in every case. The dual stage expansion mechanism facilitates the ability of the device to expand to a larger range of heights.

This disclosure contemplates that the devices (e.g., components of the devices such as the structural body, wedge blocks, linkage blocks, linkages, drive screw, etc.) described herein can be made using alternative medical grade materials. This disclosure contemplates that some or all of the components can be made of the same material in some implementations, while in other implementations some or all of the components can be made of different materials. In some implementations, the device can be made of a molybdenum-rhenium (MoRe) alloy. Optionally, the MoRe alloy is Mo47.5Re. Alternatively, the alloy is optionally 99.99% pure with at least 40 weight percent (wt %) rhenium. Optionally, the alloy is optionally 99.99% pure with between 40 wt % and 99.9 wt % rhenium (e.g., 40.0 wt %, 40.01 wt %, 40.02 wt % . . . 99.88 wt %, 99.89 wt %, 99.9 wt %) and any value or range therebetween. In other implementations, the device can be made of titanium (Ti). In other implementations, the device can be made of a titanium-molybdenum (TiMo) alloy including, but not limited to, Ti-15Mo. In other implementations, the device can be made of a titanium (Ti) alloy. In other implementations, the device can be made of a cobalt-chromium (CoCr) alloy. Other example alloys that can be used are described, for example, in U.S. 2019/0008995, published Jan. 10, 2019, titled "Molybdenum Alloys for Medical Devices," the disclosure of which is expressly incorporated herein by reference in its entirety.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An expandable interbody device, comprising:
a structural body having an upper endplate and a lower endplate, wherein the upper and lower endplates are shaped to nest tightly in a closed position, wherein each of the upper and lower endplates include at least one first oblique surface;
at least one wedge block arranged between the upper and lower endplates of the structural body, wherein the at least one wedge block includes at least one second oblique surface, wherein the at least one wedge block defines a wedge block opening, the wedge block opening defining a plurality of threads;
at least one linkage block arranged between the upper and lower endplates of the structural body, wherein the at least one linkage block comprises a plurality of linkages and a shear pin disposed at a respective proximal end of each of the linkages; and
a drive screw extending through the wedge block opening of the at least one wedge block and through the at least one linkage block, wherein the drive screw is configured to rotate and engage the threads of the wedge block opening to drive the at least one wedge block such that the at least one second oblique surface of the wedge block engages the at least one first oblique surface of the upper and lower endplates to cause the upper and lower endplates of the structural body to expand from the closed position to an intermediate position, and wherein the drive screw is further configured to rotate and drive the at least one linkage block to expand the upper and lower endplates of the structural body from the intermediate position to an open position.

2. The expandable interbody device of claim 1, wherein the shear pin is configured to prevent rotation of the upper and lower endplates about an axis of the drive screw.

3. The expandable interbody device of claim 1, wherein the shear pin extends from the at least one linkage block into a portion of the at least one wedge block.

4. The expandable interbody device of claim 3, wherein the shear pin is attached to the portion of the at least one wedge block.

5. The expandable interbody device of claim 1, wherein the shear pin extends from the at least one linkage block without extending into a portion of the at least one wedge block.

6. The expandable interbody device of claim 1, wherein the upper and lower endplates comprise first oblique surfaces and the at least one wedge block comprises second oblique surfaces, and wherein the first oblique surfaces are configured to engage with the second oblique surfaces to expand the upper and lower endplates of the structural body from the closed position to the intermediate position.

7. The expandable interbody device of claim 1, wherein displacement of the at least one wedge block is configured to exclusively control expansion between the closed and intermediate positions, and wherein displacement of the at least one linkage block is configured to exclusively control expansion between the intermediate and open positions.

8. The expandable interbody device of claim 7, wherein the at least one wedge block is configured to disengage with the structural body at the intermediate position.

9. The expandable interbody device of claim 7, wherein the at least one wedge block is configured to bear load during expansion between the closed and intermediate positions.

10. The expandable interbody device of claim 7, wherein the at least one linkage block is configured to bear load during expansion between the intermediate and open positions.

11. The expandable interbody of claim 1, wherein the drive screw comprises a first threaded portion and a second threaded portion spaced apart from the first threaded portion.

12. The expandable interbody device of claim 11, wherein the first threaded portion of the drive screw is configured to engage with corresponding threads of the at least one wedge block.

13. The expandable interbody device of claim 11, wherein the second threaded portion of the drive screw is configured to engage with corresponding threads of the at least one linkage block.

14. The expandable interbody device of claim 1, further comprising a plurality of wedge blocks arranged between the upper and lower endplates and on opposite sides of the structural body, wherein each of the wedge blocks is threaded in an opposite-handed direction, and wherein the drive screw is configured to rotate and drive the wedge blocks in opposite directions.

15. The expandable interbody device of claim 1, further comprising a plurality of linkage blocks arranged between the upper and lower endplates and on opposite sides of the structural body, wherein each of the linkage blocks comprises a plurality of linkages and a shear pin, respectively, wherein each of the linkage blocks is threaded in an opposite-handed direction, and wherein the drive screw is configured to rotate and drive the linkage blocks in opposite directions.

16. The expandable interbody device of claim 1, wherein the drive screw comprises at least one driver hole.

17. The expandable interbody device of claim 1, further comprising an alignment block configured to prevent rotation of the upper and lower endplates about an axis of the drive screw.

18. The expandable interbody device of claim 1, wherein the expandable interbody device comprises a molybdenum-rhenium (MoRe) alloy.

19. The expandable interbody device of claim 18, wherein the MoRe alloy is Mo47.5Re.

20. The expandable interbody device of claim 1, wherein the expandable interbody device comprises at least 40 weight percent rhenium (Re); or wherein the expandable interbody device comprises a titanium (Ti) alloy, a titanium-molybdenum (TiMo) alloy, or a cobalt-chromium (CoCr) alloy.

* * * * *